US010849574B2

(12) United States Patent
Helm

(10) Patent No.: US 10,849,574 B2
(45) Date of Patent: Dec. 1, 2020

(54) INTERVENTIONAL IMAGING

(75) Inventor: Patrick A. Helm, Milton, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 13/166,072

(22) Filed: Jun. 22, 2011

(65) Prior Publication Data

US 2012/0330134 A1 Dec. 27, 2012

(51) Int. Cl.
*A61B 6/12* (2006.01)
*A61B 6/00* (2006.01)
*A61B 6/03* (2006.01)

(52) U.S. Cl.
CPC ................ *A61B 6/12* (2013.01); *A61B 6/032* (2013.01); *A61B 6/4007* (2013.01); *A61B 6/481* (2013.01); *A61B 6/482* (2013.01); *A61B 6/486* (2013.01); *A61B 6/4405* (2013.01); *A61B 6/508* (2013.01)

(58) Field of Classification Search
CPC . H05G 1/60; G21K 5/10; A61B 6/481; A61B 6/504; A61B 6/4476; A61B 6/545
USPC .................. 600/424, 420, 425, 426; 128/899
See application file for complete search history.

(56) References Cited

U.S. PATENT DOCUMENTS 4,459,990 A * 7/1984 Barnea .................. A61B 6/481 600/431
5,253,169 A * 10/1993 Corby, Jr. ................ A61B 6/12 382/132
5,347,570 A * 9/1994 Haaks ........................ 378/98.12
5,592,939 A 1/1997 Martinelli
5,913,820 A 6/1999 Bladen et al.
5,915,485 A 6/1999 McAtavey
5,983,126 A 11/1999 Wittkampf
6,474,341 B1 11/2002 Hunter et al.
6,674,837 B1 * 1/2004 Tasker et al. ............ A61B 6/00 378/122
6,747,539 B1 6/2004 Martinelli
6,876,724 B2 * 4/2005 Zhou et al. ................... 378/122
6,940,941 B2 9/2005 Gregerson et al.
7,001,045 B2 2/2006 Gregerson et al.
(Continued)

FOREIGN PATENT DOCUMENTS

CN 101641589 A 2/2010
EP 0545588 A2 6/1993
(Continued)

OTHER PUBLICATIONS

International Preliminary Report on Patentability and Written Opinion for PCT/US2012/043536 dated Jan. 9, 2014, claiming benefit of U.S. Appl. No. 13/166,072, filed Jun. 22, 2011.
(Continued)

*Primary Examiner* — Angela M Hoffa
*Assistant Examiner* — Helene Bor
(74) *Attorney, Agent, or Firm* — Harness Dickey

(57) ABSTRACT

An array emitter including a plurality of emitting portions can be used to individually emit selected energy, such as x-ray radiation, from the emitter ray rather than powering or emitting radiation from all portions of the emitter array. According, providing a plurality of cells within an emitter array, and selectively emitting x-rays from individual cells can allow for selection of which cells to emit x-rays from to acquire selected image data. A process is disclosed for selecting, including automatically, which portions to power to emit energy.

32 Claims, 7 Drawing Sheets

(56) References Cited

U.S. PATENT DOCUMENTS

| | | | | |
|---|---|---|---|---|
| 7,082,182 | B2 * | 7/2006 | Zhou et al. | 378/10 |
| 7,106,825 | B2 | 9/2006 | Gregerson et al. | |
| 7,108,421 | B2 | 9/2006 | Gregerson et al. | |
| 7,188,998 | B2 | 3/2007 | Gregerson et al. | |
| 7,359,484 | B2 * | 4/2008 | Qiu et al. | 378/122 |
| 7,382,852 | B2 * | 6/2008 | Edic et al. | 378/8 |
| 7,406,148 | B2 * | 7/2008 | Russinger | A61B 6/504 378/15 |
| 7,751,528 | B2 * | 7/2010 | Zhou et al. | 378/37 |
| 7,751,865 | B2 | 7/2010 | Jascob et al. | |
| 7,772,541 | B2 | 8/2010 | Froggatt et al. | |
| 7,797,032 | B2 | 9/2010 | Martinelli et al. | |
| 2002/0094064 | A1 | 7/2002 | Zhou et al. | |
| 2004/0116803 | A1 | 6/2004 | Jascob et al. | |
| 2004/0199072 | A1 | 10/2004 | Sprouse et al. | |
| 2005/0185826 | A1 * | 8/2005 | Georgescu et al. | 382/103 |
| 2007/0078325 | A1 | 4/2007 | Fuimaono et al. | |
| 2008/0200794 | A1 * | 8/2008 | Teichman et al. | 600/407 |
| 2009/0036768 | A1 | 2/2009 | Seehusen et al. | |
| 2009/0196473 | A1 * | 8/2009 | Fujii | A61B 6/481 382/128 |
| 2009/0257559 | A1 * | 10/2009 | Urushiya | A61B 6/12 378/98.12 |
| 2009/0264727 | A1 | 10/2009 | Markowitz et al. | |
| 2010/0183116 | A1 * | 7/2010 | Zaiki | 378/8 |
| 2010/0228117 | A1 | 9/2010 | Hartmann | |
| 2010/0246759 | A1 | 9/2010 | Ogura et al. | |
| 2012/0099768 | A1 | 4/2012 | Helm et al. | |
| 2012/0099772 | A1 | 4/2012 | Helm et al. | |
| 2012/0099778 | A1 | 4/2012 | Helm et al. | |

FOREIGN PATENT DOCUMENTS

| | | | |
|---|---|---|---|
| JP | 2006-070235 | A | 3/2006 |
| JP | 2007-503893 | A | 3/2007 |
| JP | 2007-530212 | A | 11/2007 |
| JP | 2009-153589 | A | 7/2009 |
| JP | 2009-178517 | A | 8/2009 |
| JP | 2009-254428 | A | 11/2009 |
| JP | 2009-538170 | A | 11/2009 |
| JP | 2010-233962 | A | 10/2010 |
| JP | 05-237082 | B2 | 7/2013 |
| KR | 2004-0085163 | A | 10/2004 |
| KR | 2006-0116236 | A | 11/2006 |
| WO | WO-03/063195 | A1 | 7/2003 |
| WO | 2005-094688 | A1 | 10/2005 |
| WO | WO-2007-135609 | A2 | 11/2007 |
| WO | WO-2009050626 | A1 | 4/2009 |

OTHER PUBLICATIONS

Second Office Action for Chinese Patent Document No. 201280040773.1 dated Dec. 8, 2015.

First Office Action for Chinese Patent Document No. 201280040773.1 dated Jun. 15, 2015.

First Office Action for Australian Patent Application No. 2015218552 dated Jul. 8, 2016.

Office Action for corresponding Korean Application No. 10-2014-7001655 dated Aug. 26, 2015.

Korean Office Action dated Feb. 29, 2016 for Korean Application No. 10-2014-7001655 with English translation.

Office Action for corresponding Japanesse Application No. 2014-517159 dated Mar. 24, 2016 with English translation.

Office Action for corresponding Chinese Application No. 201280040773.1 dated May 12, 2016 with English translation.

Office Action for corresponding Korean Application No. 10-2014-7001655 dated Aug. 26, 2015 with English translation.

Japanese Office Action dated Jan. 13, 2017 for JP Application No. 2014-517159 corresponding to PCT/US2012/043536 claiming benefit of U.S. Appl. No. 13/166,072, filed Jun. 22, 2011.

Japanese Office Action dated Mar. 12, 2018 in corresponding Japanese Application No. 2017-078819.

European Office Action dated May 8, 2018 in corresponding European Application No. 12737377.7.

Australian Office Action dated Jun. 23, 2017 in corresponding Australian Application No. 2015218552.

Australian Patent Examination Report No. 1 for Australian Application No. 2012272869 dated Sep. 8, 2014 corresponding to PCT/US2012/043536 claiming benefit of U.S. Appl. No. 13/166,072, filed Jun. 22, 2011.

International Search Report and Written Opinion for PCT/US2012/043536 dated Mar. 11, 2012, claiming benefit of U.S. Appl. No. 13/166,072, filed Jun. 22, 2011.

Japanesse Office Action for JP Application No. 2014-517159 dated Mar. 28, 2016 with English translation.

* cited by examiner

INTERVENTIONAL IMAGING

FIELD

The subject disclosure relates to interventional procedures, and particularly to a system for imaging a subject.

BACKGROUND

This section provides background information related to the present disclosure which is not necessarily prior art.

Procedures can be performed on various subjects and structures, such as a human anatomy or other animal anatomies. The procedures, however, may generally be either open procedures or closed or less invasive procedures. In an open procedure, the anatomy of the subject is open for viewing by a surgeon. In a less invasive procedure, however, it can be selected to lessen or minimize the access or viewing of the internal portions of the subject. It may be selected, therefore, to use imaging to assist in performing a less invasive procedure.

Images of the subject can be used to assist in performing a procedure by illustrating the internal structure of the subject. Various tracking and navigation systems can be used to assist in locating and illustrating the location of the instrument relative to the structure by displaying an icon relative to the image. For example, an icon representing an instrument can be super imposed on the image of the structure of the subject to illustrate the location of the instrument relative to the subject.

The instrument can be passed through the subject at various entry locations, angles, and depths relative to the subject. Images can be obtained of the subject to assist in confirming a selected location of the instrument within the subject. Accordingly, image data of the subject can be acquired prior to performing a procedure and during a procedure.

SUMMARY

This section provides a general summary of the disclosure, and is not a comprehensive disclosure of its full scope or all of its features.

During a selected procedure, images of a subject may be acquired. Images of a subject can include images of a patient acquired during the surgical procedure. As an example, during a surgical procedure a catheter may be moved through a vascular system of a patient and images can be acquired to view or indicate the location of the catheter within the patient. The images can include appropriate imaging modalities such as MRI, computed tomography, or fluoroscopy.

Using various imaging techniques, such as fluoroscopy, obtaining or determining the location of the catheter within the patient can include moving the imaging device relative to the patient. Alternatively, it may require irradiating a patient with all of an emitter portion. According to various embodiments, however, an array emitter can include a plurality of emitting portions or cells that can be used to individually emit x-ray radiation from an emitter ray rather than powering or emitting radiation from all cells of an emitter array. Accordingly, providing a plurality of cells within an emitter array, and selectively emitting x-rays from individual cells can allow for selection of which cells to emit x-rays from to acquire selected image data.

A procedure can include movement of a catheter through a patient. Accordingly, a portion of the catheter may move or at least sequentially move relative to the patient. For example, once a catheter passes through a portion of a vasculature of the patient, generally the catheter will remain within the vasculature of the patient and only the tip or most leading end of the catheter will change position relative to the patient over time. Accordingly, it may be selected to image only the region that will change over time, such as the leading end of the catheter or where the leading end of the catheter is selected to move subsequent to a previous image acquisition. In addition, contrast can be used to image portions of the vascular. Accordingly, it may be selected to image only the portions of the patient where the contrast agent has not yet passed or entered.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The subject disclosure relates generally to performing a procedure on a subject, which can include a human subject. It will be understood, however, that the subject can include any appropriate subject where a procedure can be planned or performed to move an instrument from an exterior of the subject into an interior of the subject. The subject can include various animate or inanimate objects. For example, it can be selected to move an instrument from exterior to a shell or casing of an automotive or electronic system without removing large portions of the system to reach internal portions. Images of the selected subject system can be acquired and trajectories can be planned to move an instrument from the exterior to the interior of the subject and to perform a function, such as repair or removal of a selected component within the inanimate object. Accordingly, it will be understood that the subject disclosure is not limited to performing a procedure on a human anatomy, but rather that the subject disclosure is related generally to a procedure and/or imaging of any appropriate subject.

Figure 1:
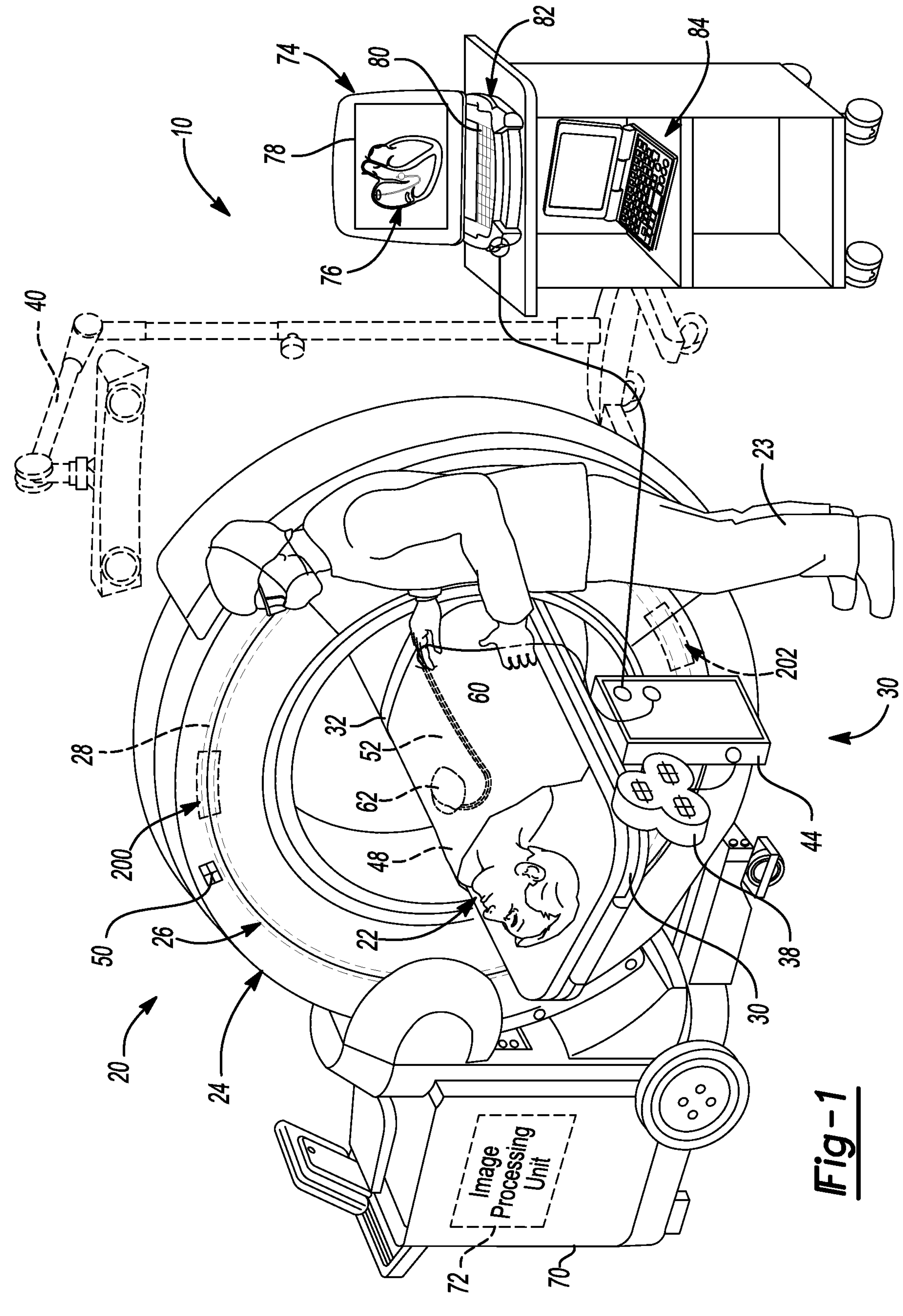
FIG. 1 is an overview of a planning algorithm and procedure.

FIG. 1 is a diagram illustrating an overview of a navigation system 10 that can be used for various procedures. The navigation system 10 can be used to track the location of an item, such as an implant or an instrument, and at least one imaging system 20 relative to a subject, such as a patient 22. A user, such as a surgeon or clinician 23 can perform or assist in performing the procedure. It should be noted that the navigation system 10 may be used to navigate any type of instrument, implant, or delivery system, including: guide wires, arthroscopic systems, ablation instruments, stent placement, orthopedic implants, spinal implants, deep brain stimulation (DBS) probes, etc. Non-human or non-surgical procedures may also use the navigation system 10 to track a non-surgical or non-human intervention of the instrument or imaging device. Moreover, the instruments may be used to navigate or map any region of the body. The navigation system 10 and the various tracked items may be used in any appropriate procedure, such as one that is generally minimally invasive or an open procedure.

The navigation system 10 can interface with or integrally include an imaging system 20 that is used to acquire pre-operative, intra-operative, or post-operative, or real-time image data of the patient 22. It will be understood, however, that any appropriate subject can be imaged and any appropriate procedure may be performed relative to the subject. The navigation system 10 can be used to track various tracking devices, as discussed herein, to determine locations of the patient 22. The tracked locations of the patient 22 can be used to determine or select images for display to be used with the navigation system 10.

Figure 2:
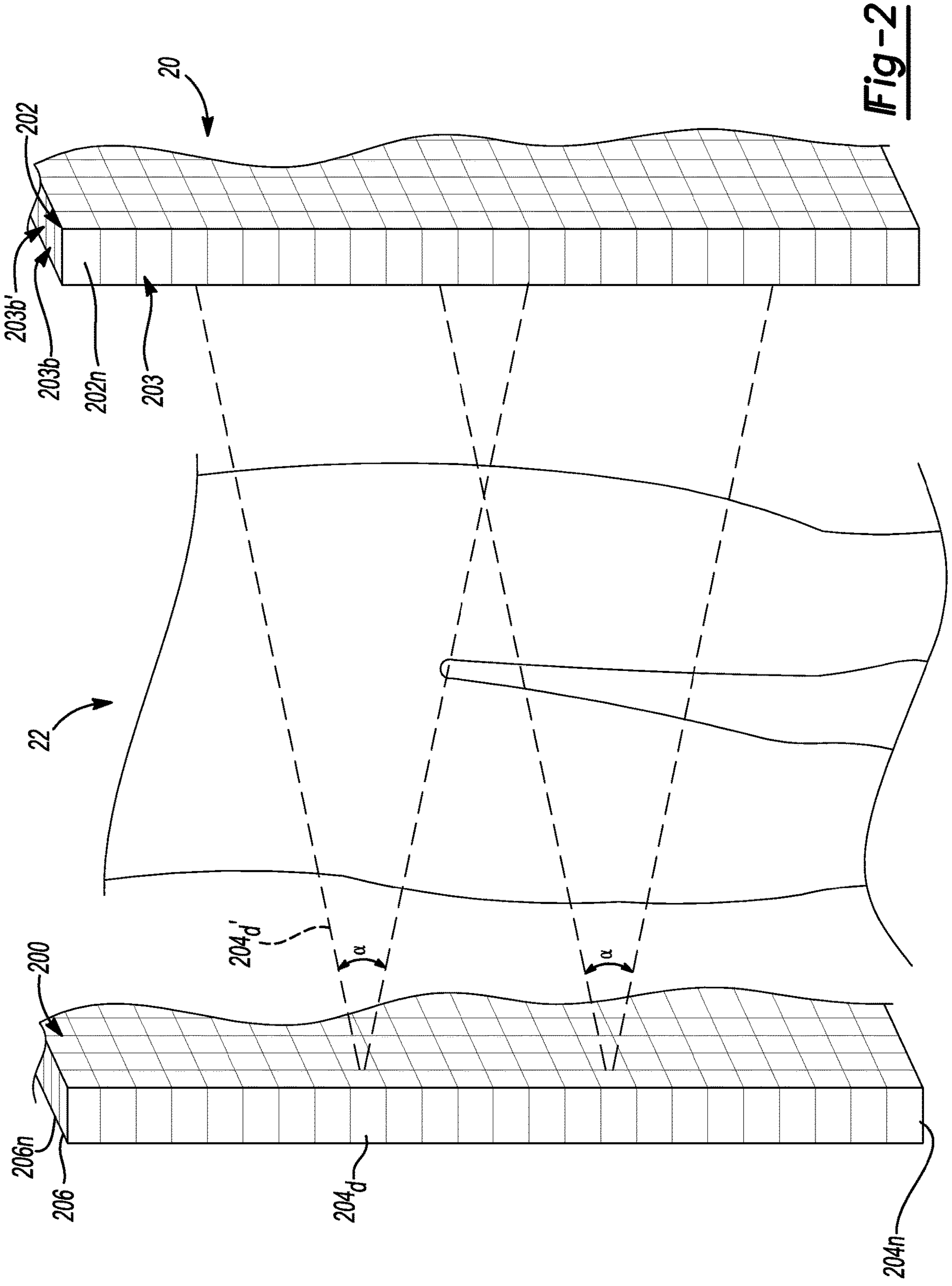
FIG. 2 is a schematic illustration of an emitter array and a detector array, according to various embodiments.

The imaging system 20 can comprise an O-arm® imaging device sold by Medtronic Navigation, Inc. having a place of business in Louisville, Colo., USA. The imaging device 20 includes imaging portions such as a generally annular gantry housing 24 that encloses an image capturing portion 26. The image capturing portion 26 may include an x-ray source or emission array portion having one or more x-ray emitting sources 200 and an x-ray receiving or image receiving array portion 202. The emission portion 200 and the image receiving portion 202 are schematically illustrated in FIG. 2. The emission portion 200 and the image receiving portion 202 are generally spaced about 180 degrees from each other and/or mounted on a rotor (not illustrated) relative to a track 28 of the image capturing portion 26. The image capturing portion 26 can be operable to rotate 360 degrees during image acquisition. The image capturing portion 26 may rotate around a central point or axis, allowing image data of the patient [[24]] 22 to be acquired from multiple directions or in multiple planes. In various embodiments each of the emission portion 200 and the receiving portion 202 can form about 180 degrees around a center or axis.

The imaging system 20 can include those disclosed in U.S. Pat. Nos. 7,188,998; 7,108,421; 7,106,825; 7,001,045; and 6,940,941; all of which are incorporated herein by reference. The imaging system 20 can, however, generally relate to any imaging system that is operable to capture image data regarding the subject 22. The imaging system 20, for example, can include a C-arm fluoroscopic imaging system, and computer tomography imagers which can also be used to generate three-dimensional views of the patient 22.

The patient 22 can be fixed onto an operating table 30, but is not required to be fixed to the table 30. The table 30 can include a plurality of straps 32. The straps 32 can be secured around the patient 22 to fix the patient 22 relative to the table 30. Various apparatuses may be used to position the patient 22 in a static position on the operating table 30. Examples of such patient positioning devices are set forth in commonly assigned U.S. patent application Ser. No. 10/405,068, published as U.S. Pat. App. Pub. No. 2004-0199072 on Oct. 7, 2004, entitled "An Integrated Electromagnetic Navigation and Patient Positioning Device", filed Apr. 1, 2003 which is hereby incorporated by reference. Other known apparatuses may include a Mayfield® clamp.

The navigation system 10 includes at least one tracking system. The tracking system can include at least one localizer. In one example, the tracking system can include an EM localizer 38. The tracking system can be used to track instruments relative to the patient 22 or within a navigation space. The navigation system 10 can use image data from the imaging system 20 and information from the tracking system to illustrate locations of the tracked instruments, as discussed herein. The tracking system can also include a plurality of types of tracking systems including an optical localizer 40 in addition to and/or in place of the EM localizer 38. When the EM localizer 38 is used, the EM localizer 38 can communicates with or through an EM controller 44. Communication with the EM controller 44 can be wired or wireless.

The optical tracking localizer 40 and the EM localizer 38 can be used together to track multiple instruments or used together to redundantly track the same instrument. Various tracking devices, including those discussed further herein, can be tracked and the information can be used by the navigation system 10 to allow for an output system to output, such as a display device to display, a position of an item. Briefly, tracking devices, can include a patient or reference tracking device (also referred to as a dynamic reference frame (DRF) to track the patient 22) 48, an imaging device tracking device 50 (to track the imaging device 20), and an instrument tracking device 52 (to track an instrument 60), allow selected portions of the operating theater to be tracked relative to one another with the appropriate tracking system, including the optical localizer 40 and/or the EM localizer 38. The reference tracking device 48 can be positioned within the patient 22 or on a surface or connected to a bone or skin, such as near a chest or connected to a tissue of a heart 62 of the patient 22.

It will be understood that any of the tracking devices 48, 50, 52 can be optical or EM tracking devices, or both, depending upon the tracking localizer used to track the respective tracking devices. It will be further understood that any appropriate tracking system can be used with the navigation system 10. Alterative tracking systems can include radar tracking systems, acoustic tracking systems, ultrasound tracking systems, and the like. Each of the different tracking systems can be respective different tracking devices and localizers operable with the respective tracking modalities. Also, the different tracking modalities can be used simultaneously as long as they do not interfere with each other (e.g. an opaque member blocks a camera view of the optical localizer 40).

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated herein by reference.

Further, for EM tracking systems it may be necessary to provide shielding or distortion compensation systems to shield or compensate for distortions in the EM field generated by the EM localizer 38. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. Pat. No. 10/649,214, filed on Jan. 9, 2004, published as U.S. Pat. App. Pub. No. 2004/0116803, all of which are incorporated herein by reference.

With an EM tracking system, the localizer 38 and the various tracking devices can communicate through an EM controller 44. The EM controller 44 can include various amplifiers, filters, electrical isolation, and other systems. The EM controller 44 can also control the coils of the localizer 40 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TRIA®, TREON®, and/or S7™ Navigation System having an optical localizer, similar to the optical localizer 40, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 20 can further include a support housing or cart 70 that can house a separate image processing unit 72. The cart 70 can be connected to the gantry 24. The navigation system 10 can include a navigation processing system or unit 74 that can communicate or include a navigation memory from which image data, instructions, surgical plans (including trajectories), and other information can be recalled. The navigation processing unit 74 can include a processor (e.g. a computer processor) that executes instructions to determine locations of the tracking devices based on signals from the tracking devices. The navigation processing unit 74 can receive information, including image data, from the imaging system 20 and tracking information from the tracking systems, including the respective tracking devices and/or the localizers 38, 44. Image data can be displayed as an image 76 on a display device 78 of a workstation or other computer system 80 (e.g. laptop, desktop, tablet computer which may have a central processor to act as the navigation processing unit 74 by executing instructions). The computer system 80 can also include the navigation memory system. The workstation 80 can include appropriate input devices, such as a keyboard 82. It will be understood that other appropriate input devices can be included, such as a mouse, a foot pedal or the like which can be used separately or in combination. Also, all of the disclosed processing units or systems can be a single processor (e.g. a single central processing chip) that can execute different instructions to perform different tasks.

The image processing unit 72 can process image data from the imaging system 20. The image data from the image processor can then be transmitted to the navigation processor 74. It will be understood, however, that the imaging systems need not perform any image processing and the image data can be transmitted directly to the navigation processing unit 74. Accordingly, the navigation system 10 may include or operate with a single or multiple processing centers or units that can access single or multiple memory systems based upon system design.

In various embodiments, the position of the patient 22 relative to the imaging system 20 can be determined by the navigation system 10 with the patient tracking device 48 and the imaging system tracking device 50 to assist in registration. Accordingly, the position of the patient 22 relative to the imaging system 20 can be determined. Other registration techniques can also be used, including those generally known in the art to register a physical space defined relative to the patient 22 to image space defined by the image 76 displayed on the display device 78.

Manual or automatic registration can occur by matching fiducial points in image data with fiducial points on the patient 22. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published as U.S. Pat. App. Pub. No. 2010/0228117, incorporated herein by reference.

Either provided with or operable to communicate with the navigation system may be a separation processing system that can include a planning system 84. The planning system 84 can include a computer processor (e.g. a central processing unit) to execute instructions based to assist in planning a procedure. As discussed here, procedures can include neural, vascular, or orthopedic procedures. The planning processor 84 can be used prior to the procedure time to plan at least a portion, such as a trajectory of an instrument for performing the procedure. Also, or in addition thereto, the planning processor can include the image acquisition algorithm, as discussed herein. Accordingly, the planning processor 84 can assist processing algorithms or information in addition to the imaging processor 72 and the navigation processor system 74 during a procedure. It will be understood, however, that all of the various processors can be included or provided as a single physical processor where each processor system includes different instruction sets executed by the same processor system.

With continuing reference to FIG. 1 and further reference to FIG. 2 the imaging device 20 will be more specifically discussed. The imaging device 20, discussed above, can be provided according to any appropriate imaging device. In addition to the O-Arm® imaging device currently sold by Medtronic, Inc., image devices can include those developed and sold by Xintek, Inc. and/or Xinray Systems, LLC. In addition, the O-ARM® imaging system or other appropriate imaging systems can include the x-ray source or emitter array 200 and the x-ray detector array or panel 202 similar to the array panels disclosed in U.S. Pat. No. 7,359,484 and U.S. Pat. App. Pub. No. 2002/0094064 published on Jul. 18, 2002, both incorporated herein by reference and schematically illustrated in FIG. 2 and discussed below.

Generally, x-rays may emit for any one or plurality of x-ray cells or portions 204. The number of the cells 204 can be an appropriate number and may differ based on the size of the array or the imaging system. Thus, a cell 204*n* can refer to any or the "last" or highest numbered cell in a series. It will be understood, however, herein specific cells may be given specific designations as specifically noted. Each cell 204 of the emitter array 200 can be defined by a carbon tube (e.g. a carbon nano-tube). The array 200 can be understood to be a linear array (e.g. substantially one dimensional having a single column 206 of the cells 204), but may also be a planar array (e.g. substantially two dimensional having both multiple columns and rows of the cells 204) that includes a plurality of columns 206*n*. Again, it is understood the specific number of the columns 206 is not required and 206*n* can reference to any number of the columns of the "last" or highest numbered column in a series. Each column 206 can include a plurality of the cells 204 and each row (as viewed defined by the cells 204 in rows as defined between columns 206 and 206*n*) of the planar array can include a plurality of the cells 204. Each cell can be provided to selectively emit x-rays through the patient or subject 22. Accordingly, the x-ray array emitter 200 can include at least a first column 206 to any number of columns 206*n*. Only a limited number of complete columns are illustrated for only simplicity and not a limiting number of columns.

Regardless, any single one of the cells or portions 204 of the x-ray emitter array 200 can emit x-rays through the patient 22 to be detected by the x-ray detector portion 202. It will be understood that the x-ray detector portion can also include or have a surface area defined by more than just a single row or column of detector portions and more than a single column of detector portions. The x-ray detector portion 202 can include a plurality of detector cells 202*n* which can be positioned in one or more rows 203*a* and/or one or more columns 203*b*. Again, only a limited number of complete columns 203*b* and 203*b*' are illustrated for simplicity.

As exemplary illustrated in at least FIG. 2, the x-ray emitter array 200 can be selected or activated to emit x-rays from a selected cell such as, for example, cell 204*d*. The x-rays generally emit as a cone from the cell 204*d* that include a selected or inherent cone angle α. The cone angle α generally allows the x-rays to pass through the patient 22 and excite a selected portion or all of the x-ray detector 202. As illustrated, however, only a portion of the x-ray detector 202 may be irradiated with the x-ray energy from the selected x-ray emitter 204*d* and, also, only a portion of the patient within the cone 204*d*'. Accordingly, energizing or selecting a different cells 204 to emit x-rays, such as 204*n* even if it has the same angle α of the cone can irradiate a different portion of the patient 22 then when the first cell 204*d* is powered to emit x-ray radiation. Also, a different projection (i.e. angle of incidence of x-rays through the patient 22) is achieved at each of the different cells 204. In other words, a ray that defines a center of the cone of x-rays can be different relative to the patient 22 from each of the cells 204.

Using the understanding that the x-ray emitter 200 can emit x-rays from selected numbers of the cells 204 selectively to irradiate the patient 22, the following discussion is directed to selectively, either automatically or with the user 23 intervention, to determine which selected portion of the x-ray emitter array 202 to power to irradiate the patient 22 to generate image data at different times. The image data generated with the imaging device 20 can be used for various purposes, such as reconstruction of the patient, including generating three dimensional reconstructions, including volumetric three dimensional reconstructions based on a plurality of two dimensional image data (where the image data includes a set of image data information regarding the image). The three dimensional reconstructions can reconstruct the patient 22 in three dimensions even though only two dimensional images are acquired by the imaging device. By acquiring views of the patient 22 at different locations, a reconstruction of the patient 22, or portion of the patient 22, in three dimensions for viewing on the display device can be made. Exemplary appropriate three-dimensional reconstruction techniques are disclosed in both U.S. patent application Ser. No. 12/908,189, filed on Oct. 20, 2010; U.S. Pat. No. 12/908,195, filed on Oct. 20, 2010; and U.S. patent application Ser. No. 13/016,718, filed on Jan. 28, 2011; all incorporated herein by reference. Reconstruction can be based upon various techniques to reconstruct portions of the patient and substantially three dimensions for viewing by user 23 on the display device 78.

Image data can be acquired at different times by powering different ones of the cells 204 to generate different projections of image data. The different projections can be used to view movement or change within the patient 22, such as due to movement of the instrument 60. The reconstruction, however, can be a three dimensional reconstruction, as discussed above. The three dimension reconstruction can be based on a plurality of image projections that are two dimensional and acquired with the imaging device 20. Reconstruction systems and methods include those incorporated above. Reconstructions, as discussed herein, can use additional data acquired with the imaging system and compared to a previous reconstruction, automatically or with user intervention. Also, an updated reconstruction can be based on a weighted matrix where a pixel or voxel in the reconstruction includes a weighted amount of data from a later acquired projection acquisition after a version of the model was reconstructed based on previous image data.

Figure 3A:
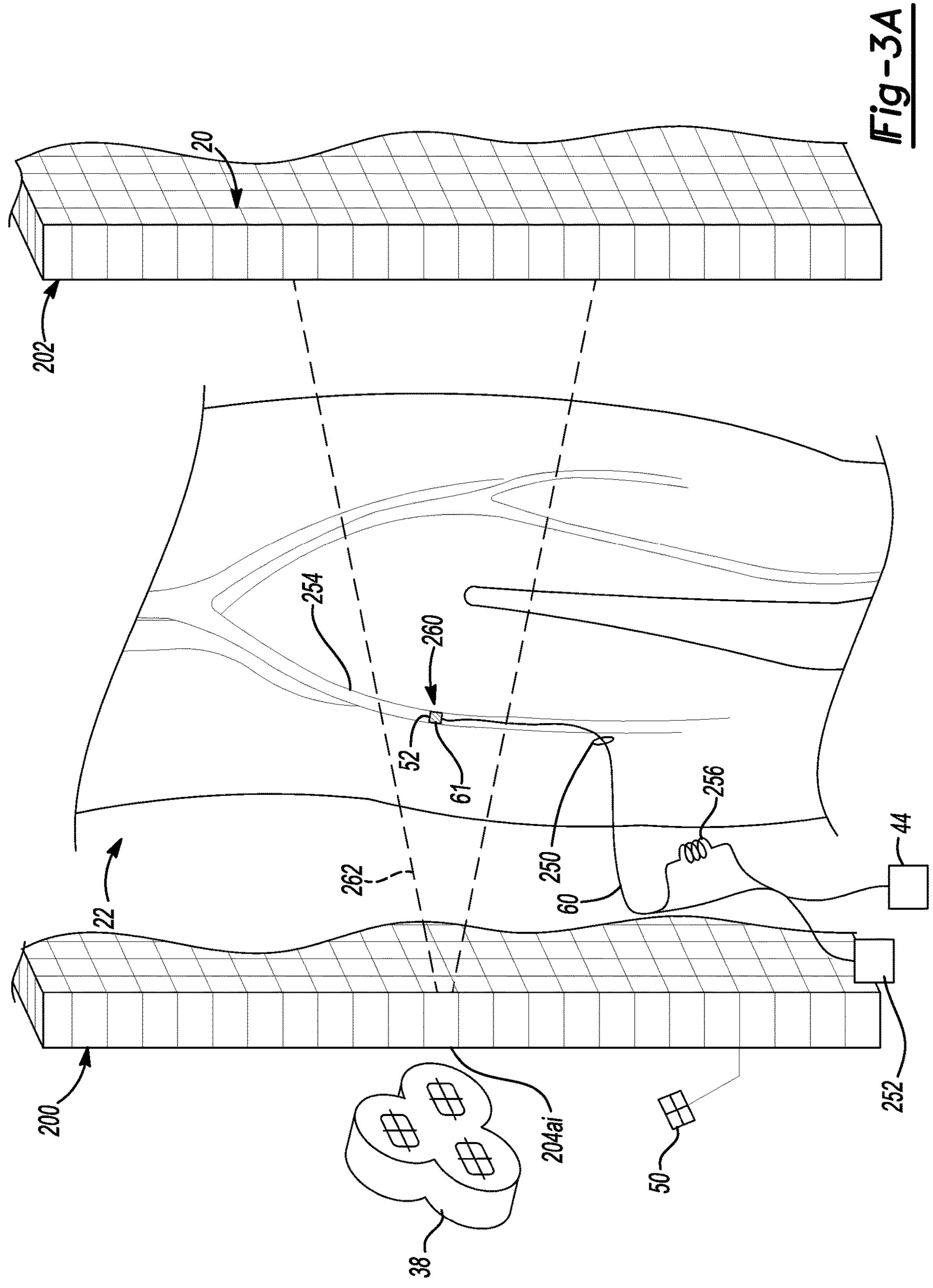
FIG. 3A is a schematic illustration of an acquisition of image data at a first time.
Figure 3B:
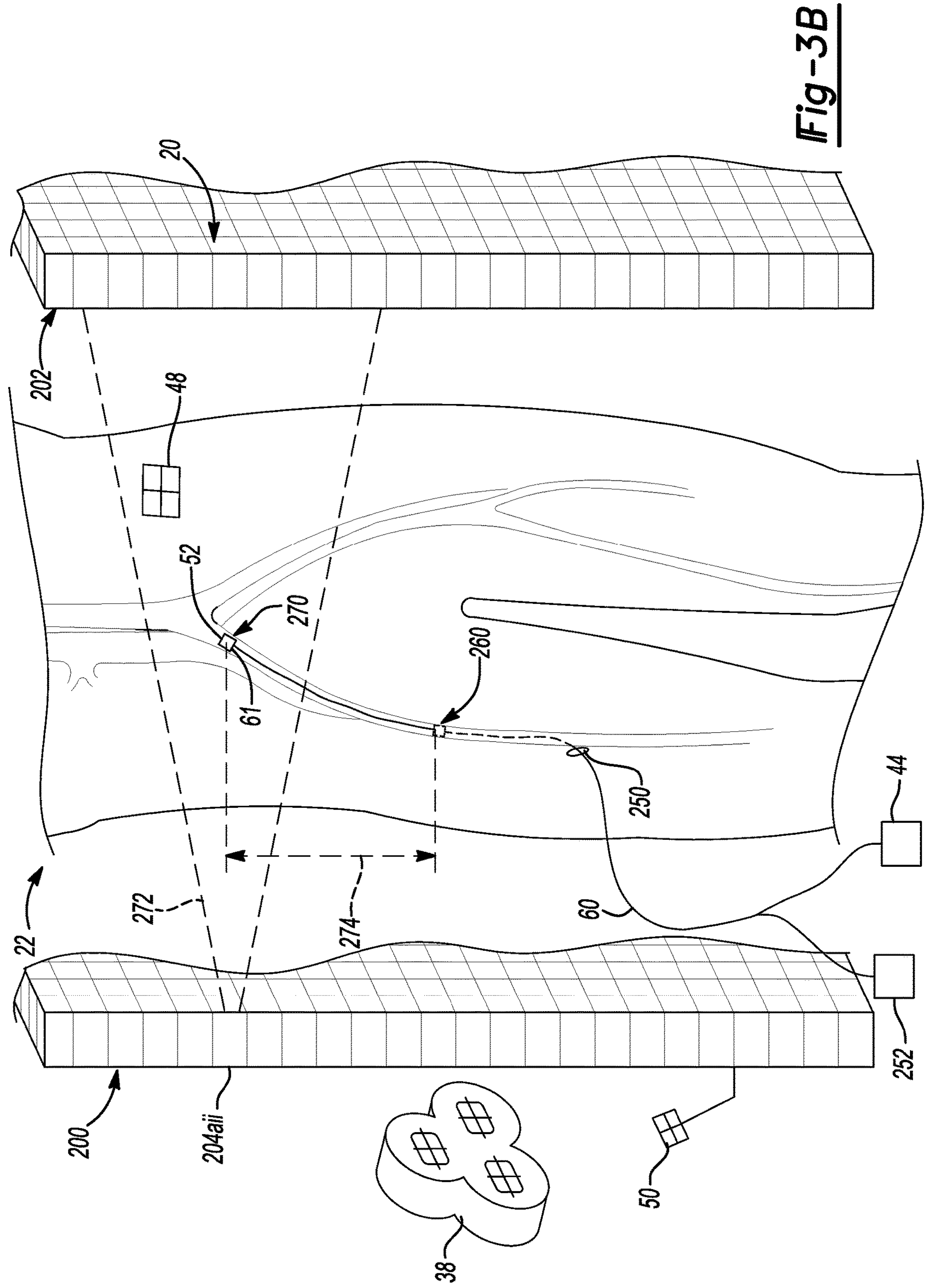
FIG. 3B is a schematic illustration of image data of an instrument at a second time.

With references to FIGS. 3A and 3B, according to various embodiments, the instrument 60 can be passed into the patient 22 in a selected manner, such as through an incision or opening 250 in the patient 22. At different times different cells 204, such as cell 204*ai* and 204*aii*, can be used to emit x-rays. The catheter 60 can be any appropriate catheter, such as one for delivering a therapy to the patient 22. For example, the catheter can be an ablation catheter, a drug delivery catheter, or other appropriate catheter that can be positioned within the patient, such as relative to or in the heart 62 of the patient 22 to deliver a therapy, such as ablation or drug therapy. Accordingly, the catheter 60 can be interconnected or connected to a therapy delivery device 252 which can include an ablation system (e.g. RF ablation system) or drug delivery system (e.g. a drug delivery reservoir or pump). The catheter 60, therefore, can be an appropriate catheter including one that can transmit or deliver the RF energy to a selected portion of the patient 22 or include various cannulas for delivering the drug therapy to the patient 22.

The catheter 60 can also include the instrument tracking device 52 which can include an appropriate tracking device, such as an electromagnetic tracking device that can sense or emit an electromagnetic field. The electromagnetic tracking device can include those associated with or used in the Axiem® Stealth Station System sold by Medtronic Navigation, Inc., discussed above. Other tracking systems can also be used with the catheter 60. For example, a shape detection or determination system can include a fiber-optic shape determination system. An appropriate fiber-optic shape determination system include that disclosed in U.S. Pat. No. 7,772,541, issued on Aug. 10, 2010 and incorporated herein by reference. In addition, tracking systems can include an electro-potential tracking system as disclosed in U.S. patent application Ser. No. 12/421,332, filed Apr. 9, 2009 and published as U.S. Pat. App. Pub. No. 2009/0264727, incorporated by reference. Regardless of the tracking device, the catheter 60 can also be interconnected with the instrument interface 44. It will be understood that the instrument interface 44 can interface with the electromagnetic system, as specifically discussed above, or can interface within an appropriate transmission or information system that can determine or transmit tracking information to the navigation processor system 74 of the navigation system 10. It will be understood that the information transmitted from the instrument interface 44 to the navigation system processor 74 can be wired or wireless, as selected for transmitting the location information.

Regardless, the tracking device 52, as discussed herein, can relate to any appropriate tracking system and discussion of an EM tracking device is merely exemplary. Nevertheless, the tracking device 52 can be used to determine the position of at least a portion of the catheter 60, such as a distal or leading tip 61. The leading end tip 61 of the catheter 60 generally moves within a vasculature 254 of the patient to a selected location, such as within the heart 62 or near the heart 62 of the patient 22, as illustrated in FIG. 1. Also, the location of the leading tip 61 of the catheter can be based upon analysis of the shape and orientation of the tip 61. For example, a particular movement or orientation of the tip 61 can be used to determine a location of the tip within the heart of the patient 22.

The leading end 61 generally moves relative to the patient while the trailing portion of the catheter can be let out or pushed into the patient 22 from a catheter supply source 256. The catheter supply source 256 can simply be a portion of the catheter not yet positioned within the patient 22 or it can be any appropriate delivery or supply source. Regardless, as the catheter 60 is laid out or fed out into the vasculature 254 of the patient 22, generally only the portion of the patient 22 near the leading end of the catheter 61 will change over time as the catheter 60 is moved within the patient 22.

As specifically illustrated in FIG. 3A, the catheter 60 has been introduced into the patient and moved a selected distance within the vasculature 254 of the patient. As illustrated, the leading end 61 is at a point or position 260 within the patient 22. The point 260 can be defined by the patient 22 and can include any geometric relationship relative to the patient 22. Nevertheless, a cone of x-rays emitted from cell **204*ai* can generate a cone of x-rays 262 that may encompass or include the point 260 of the patient 22. The x-rays emitted from the cell 204*ai* can be detected by the x-ray detector 202 of the imaging system 20. This can be used to generate image data at an initial time or first time $t_0$. Also, the location of the catheter 60 can be determined by tracking the location of the tracking device 52 and the location can be determined or analyzed with the navigation processing system 74. The determined location of the catheter 66, patient 22, and imaging device 20 can be used to determine which cells 204** to power to emit x-rays, as discussed herein.

With the additional reference to FIG. 3B, the catheter 60 can be continued to be fed into the patient 22 for a selected period or until the catheter 60, in particular the leading end 61, has moved to a selected location. Accordingly, after a selected time, such as a time delta, the leading end 61 of the catheter can move from the initial or first position as illustrated in FIG. 3A (also referred to as time zero or $t_0$) to a second or later location at position 270. Again, position 270 can be defined as a geometrical location relative to the patient and can be at a different physical location from the position 260 relative to the patient 22.

As illustrated in FIG. 3B, the catheter 60 has been moved into the patient such that the leading end 61 has moved from the position 260 to the position 270. However, the portion of the patient where the catheter had already been laid out in the patient 22 when the leading end 61 was at position 260 remains substantially unchanged for imaging purposes. Accordingly, it can be selected to emit x-rays from a different cell, for example different from cell **204*ai*, to emit a second cone of x-rays 272 to be detected by the x-ray detector 202. It will be understood that any appropriate number of the cells of the emitter array 200 can be energized or powered to emit x-rays, such as emitting x-rays to cover the entire area, distance, or position change 274 between the first position 260 and the second position 270 of the leading end 60 for the catheter 60. It is illustrated here only emitting x-rays from a second cell 204*aii*** at a second time $t_\Delta$ or $t_n$ for simplicity of this illustration.

To assist in selecting which cell 204, such as cell **204*aii*, to power the location of the leading end 61 of the catheter can be determined with the tracking device 52 associated with the catheter 60. As discussed further herein, the determined or tracked position of the tracking device 52 can be used to assist in determining which of the cells of the emitter 200 can be energized or used to emit x-rays to selectively image the position or portion of the patient 22 where the position of the catheter 60 has changed. As discussed above, the imaging device tracking device 50 can be used to track a position of the imaging device 20 and a patient reference tracking device 48 can be used to track the location of the patient 22**, if selected.

The tracked position of the imaging device 20, using the imaging device tracking device 50, and the catheter tracking device 52 can be used to identify or selectively identify which cells of the emitter ray 200 can be energized to selectively image the portion of the patient 22 including the area that possibly or does substantially changes due to movement of the catheter 60 within the patient. As discussed above, generally only the area defined by the distance or change 274 will substantially change relative to the image acquired at time $t_0$ due to movement of the catheter 60 or movement in this area as opposed to during the previous acquisition.

In addition, the image data acquired with the imaging device 20 can be used to determine which of the cells 204 to power. For example, a sample number of projections can be acquired with a selected number of the cells 204 individually powered. The sample projections can then be compared to prior projections and/or the previously reconstructed model based on previous projections. The comparison can be made with a processor, such as the processor 72 of the imaging system 20, to determine which pixels include new or changed image data (e.g. pixels that include contrast due to the presence of the catheter 60). Once the determination has been made which pixels include new or changed image data, a determination can be made as to which of the cells 204 can be powered to acquire image data necessary or selected to update the model of the patient 22 by the acquisition of new image data. The determination of what additional projections can be made by execution of the processor or with user intervention.

Again, the image data acquired with the imaging device can be used to generate a model of the patient 22. As the catheter 60 is moved, the reconstructed model can be updated with a current or near current illustration of a location (including position and orientation) of the catheter 60 by acquiring additional projections with the imaging device 20 to update the reconstructed model. It is also understood that the image projections can be viewed directly to view changes in the position of the catheter 60.

Figure 4A:
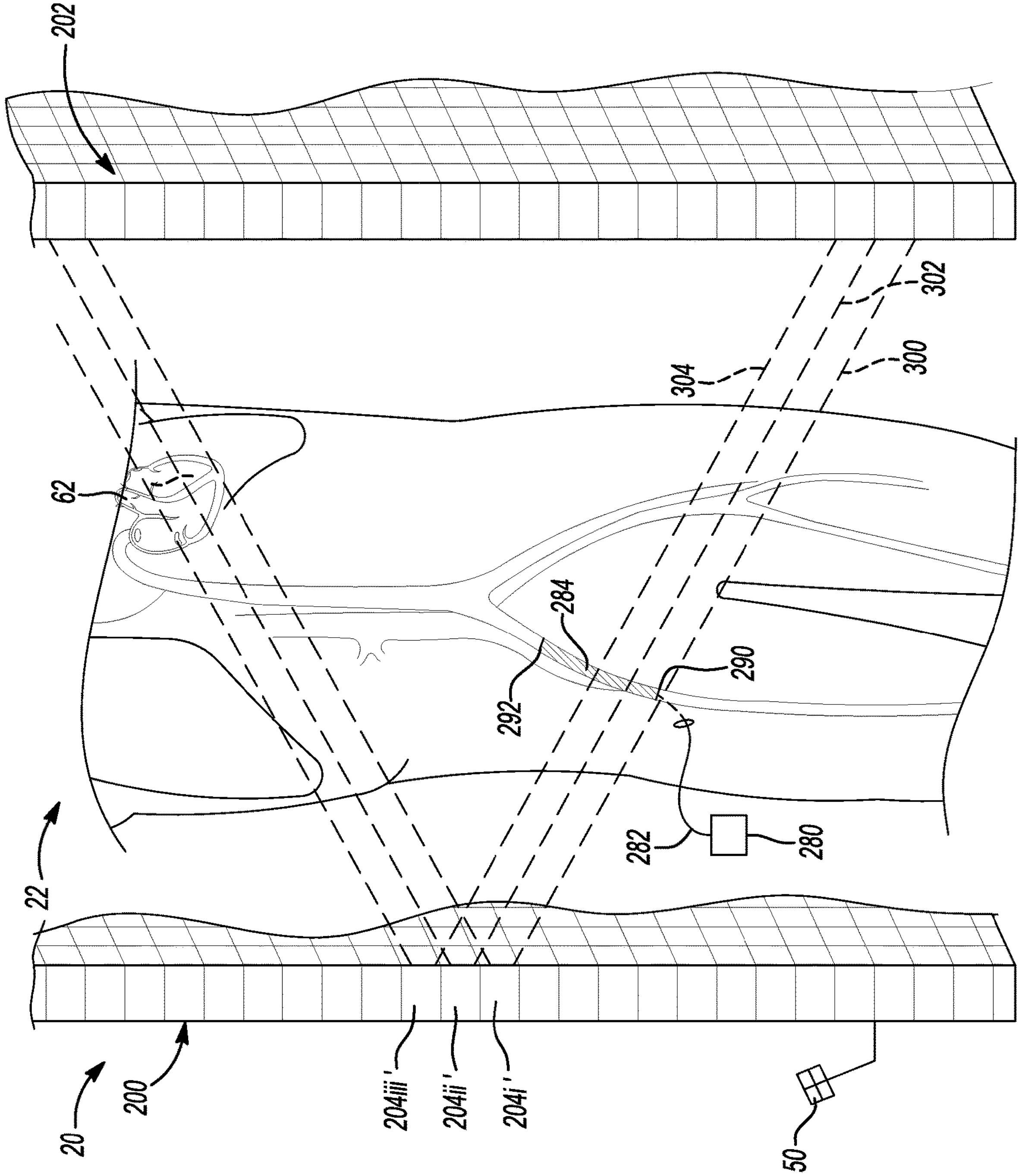
FIG. 4A is a schematic illustration of acquisition of image data of a subject with a contrast agent at a first time.
Figure 4B:
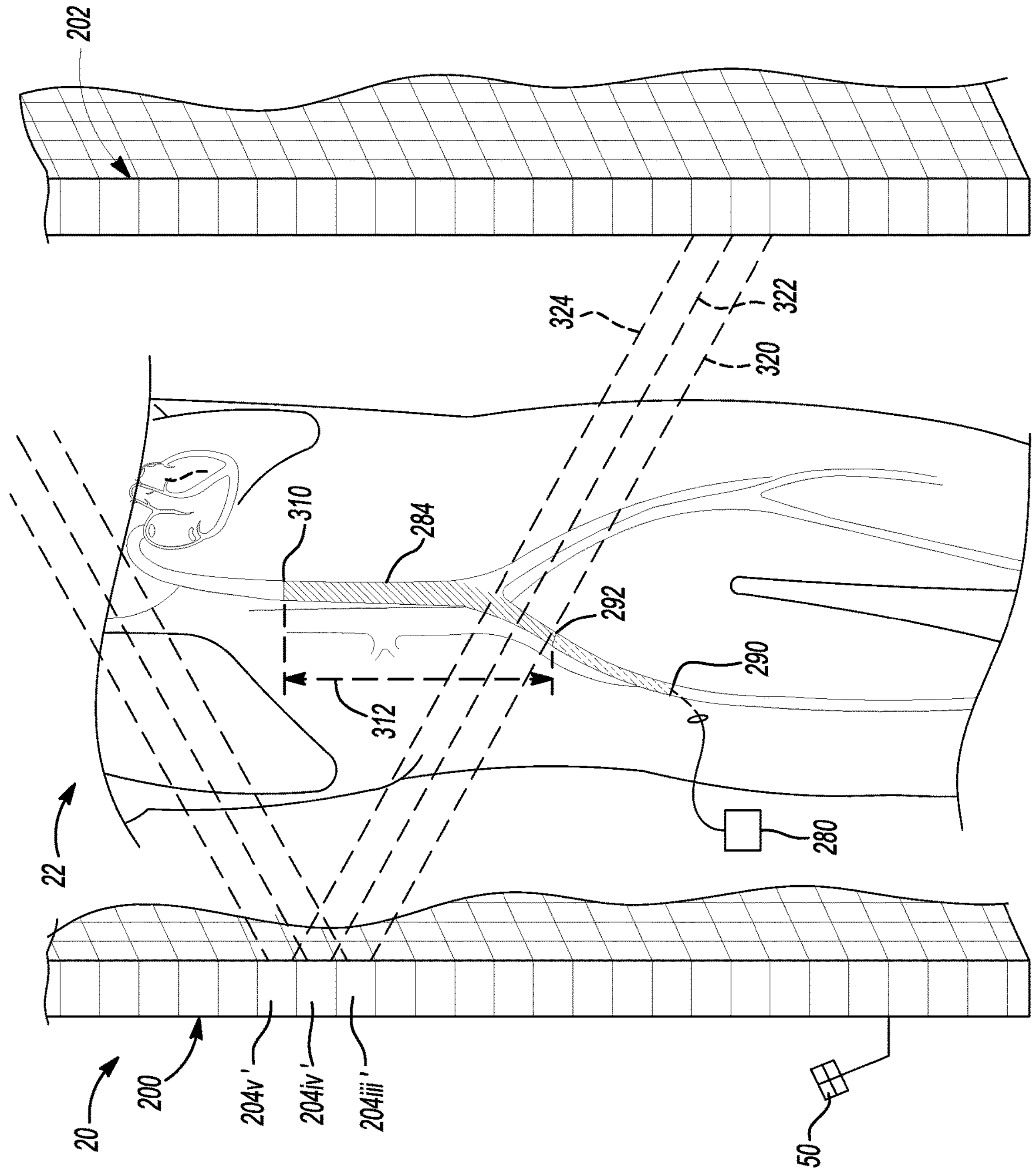
FIG. 4B is a schematic illustration of acquisition of image data of a subject with a contrast agent at a second time.

As a further example, and with reference to FIGS. 4A and 4B, a contrast agent can be injected into the patient 22. The contrast agent can move within the patient 22 from a first time period, such as when a first image data is acquired at time $t_0$ (as illustrated in FIG. 4A) to a second time (e.g. time $t_n$ or $t_\Delta$) in FIG. 4B. As discussed herein, the contrast agent can move through a vasculature 284 of the patient 22 to be imageable by x-ray radiation.

With the initial reference to FIG. 4A, a contrast source 280 can be used to inject the contrast agent into the patient 22. The contrast agent can be injected through a delivery tube or portion 282 into the vasculature 284 of the patient. As exemplary illustrated in FIG. 4A, the contrast agent delivered into the vasculature 284 can begin to travel through the vasculature via the flow of blood through the vasculature of the patient 22. As exemplary illustrated, the contrast agent has traveled from a first point or position at the entry of the delivery device 290 to a second end or a leading end point 292. It can be selected to image the patient 22 with all of the cells of the emitter array 200 or selected number of the cells 204*i*', 204*ii*', 204*iii*' that can generate three cones of x-rays 300, 302 and 304. The three cones 300-304 can engage or hit the collector 202 to allow for the generation of image data with the imaging device 20. The image data can be used to generate the image of the patient 22 and the vasculature with the contrast agent therein. Generally, the area with the contrast agent between the start point 290 and the end point 292 can be used for viewing or determining configuration of the vasculature or any blockage therein. In addition, a plurality of power sources or power types can be used to power the x-ray emitter 200 at different energies to assist in enhancing contrast of the area of the patient 22 with the contrast agent and the area without the contrast agent as disclosed in U.S. patent application Ser. No. 13/016,718, filed on Jan. 28, 2011, incorporated herein by reference.

With additional reference to FIG. 4B, the contrast agent can be continued to be delivered to the patient 22 or continue to flow through the patient 22, as generally understood in the art. As discussed above, the initial point 290 where the contrast agent entered the patient 22 and the first point 292 at time $t_0$ during the acquisition or at the acquisition of the first image data can differ from the position of the contrast agent within the patient 22 or the entire area of the contrast covered area within the patient 22.

As illustrated in FIG. 4B, at time $t_n$, the contrast agent can have passed through another region to a third point 310 within the patient 22. Accordingly, an additional region 312 has been filled or can include contrast agent that was not filled with contrast agent at the initial time $t_0$. Accordingly, it can be selected to generate x-rays with different cells or at least only some of the previous cells 204 when acquiring image data at the second time or a different time $t_n$. For example, as illustrated in FIG. 4B, cells 204*iii*', 204*iv*', and 204*v*' can be used to emit x-rays in three cones 320, 322, and 324.

Accordingly, one cell 204*iii*' can be used to emit x-rays at both the initial time and the second time $t_n$. The emission of x-rays can therefore, be used to provide overlap in the image data between the previous data acquired, as illustrated in FIG. 4A at time $t_0$ and the image data acquired, as illustrated in FIG. 4B, at the time $t_n$. The additional cells can be used to acquire additional image data that allows for illustration of the movement of the contrast agent through the patient 22 over time. It will be further understood, that although each of the cells 204*iii*, 204*iv*, and 204*v* can be used to generate image data at the second time $t_n$, each cell may be used to generate x-rays in a sequence rather than all at once. Thus, the image data at the second time $t_n$ may include a plurality of quickly acquired image frames (e.g. where x-rays are detected that are emitted from only a single one of the cells 204). As is generally understood, the image data can then be used to determine a position of the contrast agent within the patient 22, by using image data analysis, including overlap of the image data and determining location or the portion of the patient 22 in which the contrast agent is present.

As illustrated in FIGS. 4A and 4B, the contrast agent does not include a tracking device associated therewith. As the contrast agent is generally a material that is flowable through the patient and is not a solid to which a tracking device can be connected. Accordingly, analysis of the image data acquired with the imaging device 20 can be used to identify a location of the contrast agent within the patient 22. Generally, a contrast analysis (e.g. indentifying pixels or voxels in the image data that have high contrast relative to surrounding pixels) can be used to identify those regions of the image data, which can relate to regions of the patient 22 that include the contrast agent.

It is understood that the image analysis can also be used to identify the portion of the patient 22 to which the contrast agent would next be travelling. As illustrated between FIGS. 4A and 4B, the cells 204 of the emitter array 202 are energized to emit x-rays along the course of travel of the contrast agent through the vascular 284 of the patient 22. Accordingly, the image processing unit 72, or an appropriate processing unit, can acquire image data of the patient 22 and determine a possible region of change between a first time and a second time that may be subsequent to the first time. The imaging processor 72 can then be used to identify the portion of the x-ray emission array 200 that should be used to emit x-rays to acquire additional imaged data of the patient 22 to image the possible region of change. For example, after the acquisition of the initial image at time $t_0$ as illustrated in FIG. 4A, cells at the two extremes, such as one just on the side of 204*i* and one on the other side of 204*iii*' can be energized to determine the position or directional change of the contrast agent within the patient 22. The selection of additional or different cells to power can also be based on projections compared to previous projections and/or a reconstruction, as discussed in relation to the catheter 60. The additional projections, therefore, can be automatically determined or determined to be used to analyze the image data compared to previous image data either individually or in the reconstructed model. After a determination is made of the change in position of the contrast agent, a selected processor can be used to determine which additional cells 204 should be energized to acquired appropriate image data of the patient 22.

Again, as discussed above, portions of the patient 22 that remain substantially unchanged between time $t_0$ and time $t_n$ need not be imaged again. For example, if imaged data is already required of the vascular 284 between the initial point 290 and the second point 292 in the image acquired at $t_0$, additional image data of the portion of the patient 22 that remains substantially unchanged need not be acquired again. Therefore substantial overlap of imaging is not required to obtain complete image data or selectively complete image data of the patient 22.

Exemplary embodiments are discussed above for selectively powering cells of the emitter array 200 to selectively and differently image the patient 22. A process for determining the portions of the emitter 200 to be used to emit additional x-rays is discussed further herein, including the flow chart 400 illustrated in FIG. 5. It will be understood that the process can be used to identify which portions of the patient require further image acquisition according to any appropriate procedure being performed, such as moving a catheter through the vasculature of the patient 22, moving a contrast agent to and/or through the patient, or performing a reconstruction of at least a portion of the patient 22. Additionally, it will be understood that other procedures can be performed including the positioning of a pedicle screw, positioning of an orthopedic implant or other appropriate procedures. Accordingly, the discussion herein relative to movement of a contrast agent or instrument through the vasculature of the patient 22 is intended to be only an example of the procedures that can be performed.

Figure 5:
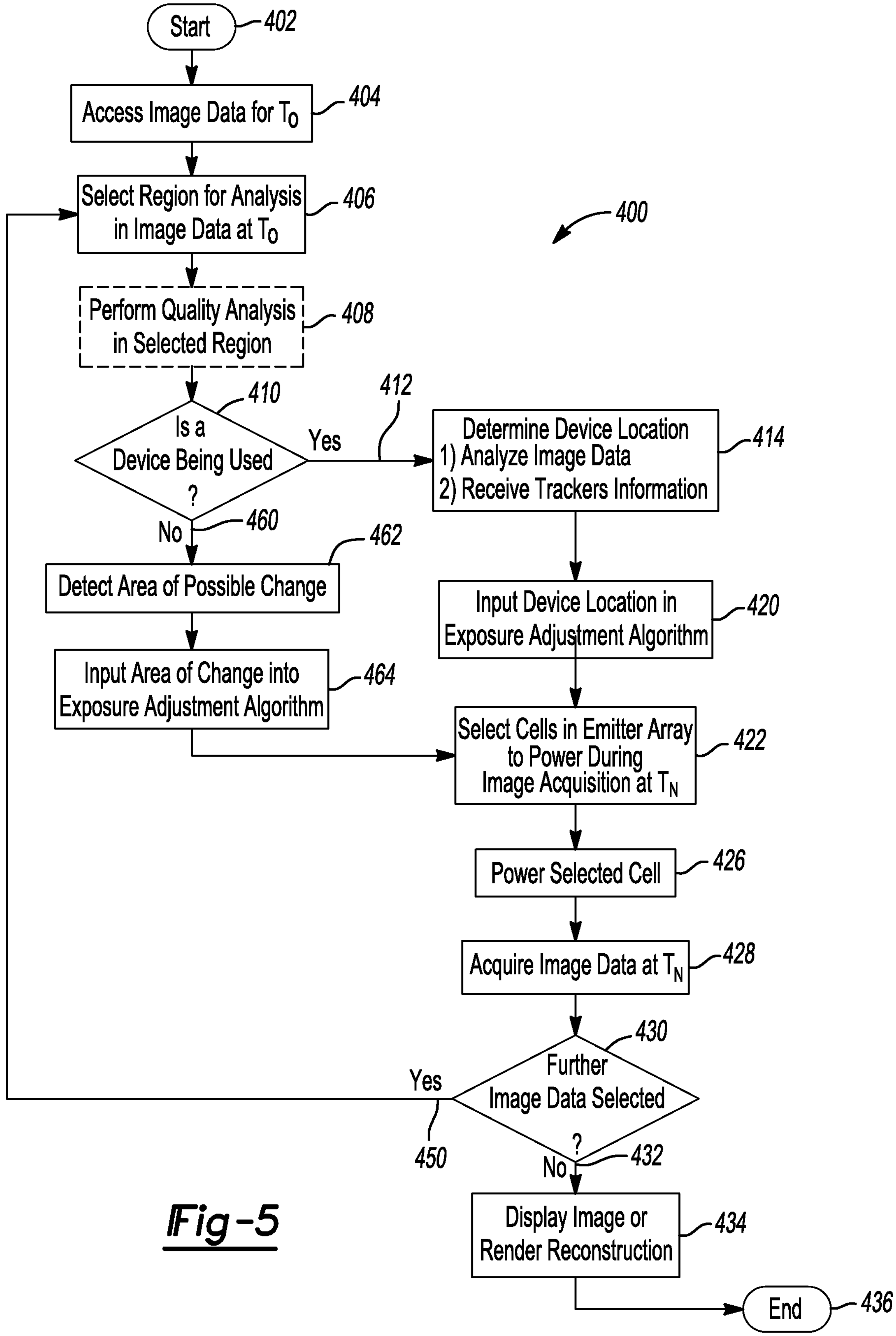
FIG. 5 is a flow chart illustrating a method of determining additional image acquisition regions.

With continuing reference to FIG. 5, the flowchart 400 can be used to determine which portion of the x-ray emitter array 200 should be powered, such as selecting particular cells 204, to acquire image data of the patient 22 for further image acquisition for further study and/or reconstruction. In a particular example, the flowchart or system starts at start block 402. Accessing image data at time $t_0$ or acquired at time $t_0$ can occur in block 404. The accessed image data from time $t_0$ can include accessing or recalling from memory image data that is acquired at an initial time or at a selected time (e.g. acquired when the request for the access of the image data is made). As discussed further herein, image data can be acquired at a second time or at a subsequent time $t_n$. The image data acquired at time $t_n$ can include image data that is acquired after any previous image data acquisition, wherein image data acquisition at time $t_0$ can simply be the image acquisition at a time before, such as immediately before the acquisition of the image data at time $t_n$.

Once the image data for time $t_0$ is acquired or accessed in block 404, a selection of a region for analysis can be made in block 406. The region of analysis selected in block 406 can be any appropriate region and can be automatically or manually selected. For example, a user, such as the surgeon 23, can view image data on the display 78, or on a display associated with the planning processor 94 or the imaging device 20, to select a region for further analysis. Alternatively, or in addition thereto, a region can be selected based upon a tracked location of an instrument (e.g. tracked with the tracking device 52) or based upon image analysis. For example, as discussed above, a contrast agent can be injected into the patient 22 and image data can be acquired at various times. The image data can be analyzed to determine the location of the contrast agent within the patient 22 in the image data at time $t_0$. Various techniques can be used to assist in determining the location of the contrast agent, such as using a dual power source emitter disclosed in U.S. patent application Ser. No. 13/016,718, filed on Jan. 29, 2011, incorporated herein by reference.

Regardless of the selection procedure, after selecting a region, a performance of a quality analysis in the selected region can be performed in block 408. It is understood that performing a quality analysis in the selected region in block 408 can be optional and is not required. According to various embodiments, image data acquired of the patient 22 can be used for performing or creating a three-dimensional reconstruction of at least a portion of the patient 22. Accordingly, performing quality analysis of the selected region in block 408 can be used to determine whether the image data acquired at time $t_0$ is appropriate for performing a reconstruction. The analysis can be used to assist in determining whether there should be additional overlap or a reacquisition of image data that substantially mimics the image data acquired at time $t_0$. Nevertheless, no quality analysis may be necessary, if, for example, it is determined that an appropriate amount of image data (e.g. substantial overlap) that a quality analysis is not necessary in block 408.

After the selected region for analysis is performed or selected in block 406, and optional quality analysis is done in block 408, a determination of whether the instrument 60 is being used in block 410 can be made. The determination can include a manual input by the user 23 to indicate whether an instrument is being used. In addition to or alternatively to a manual input, the navigation system 10 can determine whether a tracked instrument is being tracked by determining whether a tracking device 52 (or other tracking device or system) is being used. If it is determined that a device is being used in block 410, a YES path 412 can be followed to determine a location of the device in block 414.

The determination of the location of the device in block 414 can be based upon various information. For example, an analysis of the image data can be performed to determine a location of the device. As illustrated in FIGS. 3A and 3B, when the instrument 60 positioned in the patient 22 is radiopaque it may be viewable or identifiable in the image data. Accordingly, the image data can be analyzed to determine the location of the instrument 60 within the image data. The navigation system 10 can then determine the location of the instrument relative to the imaging device 20 and the patient 22. The imaging device tracking device 50 is used to determine the location of the imaging device and the patient tracking device 48 can be used to determine the location of the patient 22 relative to the imaging device 20. Also, the patient 22 may be fixed relative to the imaging device 20. The relative position of the imaging device 20 and the patient 22 can be used to determine the position of the device 60 once the device 60 is identified in the image data.

Alternatively, or in addition to image analysis, the tracking device 52 can be tracked with the tracking system, such as with the EM localizer 38, to determine a location of the instrument 60 within the patient 22. The imaging device tracking device 50 can further be used to determine the location of the instrument 60 relative to the imaging device 20, including the x-ray emitter array 200. It will be understood, however, that the tracking device can also include any appropriate tracking devices such as the electropotential tracking device, a fiber optic shape tracking device as discussed above, or other appropriate tracking devices.

Regardless of the method, the determination of a position of the instrument 60, including or limited to a position of a leading end 61 of the instrument 60, can be made. The instrument 60 is illustrated as a catheter, but can be any appropriate instrument positioned in any appropriate portion of the patient 22. The instrument 60 can include a pedicle screw inserter, a deep brain stimulation probe and/or inserter, or other appropriate instruments.

Once the location of the instrument, or appropriate portion of the instrument is made, an input of the device location into the exposure adjustment algorithm can be made in block 420. The input of the device location can be a manual input of the device location by the user 23, such as using the input device 82, or can be an automatic transference of the location information determined by the tracking system of the navigation system 10. The exposure adjustment algorithm can then use the location of the instrument or device 60 to determine or select cells of the emitter array 200 to be powered during an image acquisition at time $t_n$ in block 422. The image acquisition at time $t_n$ can include an acquisition that is substantially immediately after the acquisition of data at time $t_0$. It will be further understood, however, that the acquisition of image data at time $t_n$ can be at any appropriate time after a prior acquisition. For example, the exposure adjustment algorithm can be used to plan any appropriate number of time differential exposures.

The exposure adjustment algorithm can be any appropriate algorithm that can assist in determining which cells of the emitter array 200 to power to acquire additional image data of the patient 22. As discussed above, each of the cells 204 can emit a cone of x-rays relative to the patient 22 to be detected by the x-ray detector 202. Generally, however, the cone of x-rays from each of the different cells 204 have different angles relative to various positions of the patient 22 based upon the different locations of the cells 204 relative to the detector 202 and a ray defining a center of the cone of the x-rays passing through the patient 22. Thus, each of the cells 204 can be used to generate a different projection of image data through the patient 22. In other words, each of the cells 204 can be used to generate image data at different angles relative to the patient 22. Accordingly, the exposure adjustment algorithm can determine which of the cells 204 to power to generate additional x-rays at subsequent times to generate additional image data regarding where the instrument may pass. This can be done so that all of the cells 204 of the emitter array 200 are not powered at each image acquisition or that all of the cells need not be powered ever. By powering only a portion of the cells 204 separate and distinct projections are acquired of the patient 22. Thus, different projections can be acquired without physically moving the emitter array 200. Also, limiting the number of cells 204 powered can lower x-ray radiation exposure of the patient 22 and other staff, while still ensuring acquisition of image data at appropriate locations relative to the patient 22.

Accordingly, the exposure adjustment algorithm can include inputs from the image analysis in block 408 and determination of a position of the device in block 414 to determine which of the cells 204 should be powered for a later image acquisition. For example, further input can include a known flight of movement of the device 60 within the patient 22.

Alternatively, or in addition to the flight of movement of the position of the device, a weighting matrix can weight the pixels in the image data that relate to the different cells or pixels of the detector array 202 to determine which of the cells 204 of the emitter array 200 should be powered to acquire additional image data. For example, in making a reconstruction, the reconstruction program can generate or render a three dimension reconstruction of a portion of the patient based upon a plurality of two dimensional image acquisitions or images. The reconstruction can be made if an appropriate number of images at different positions or projections relative to the structure of the patient 22 are acquired. Accordingly, by generating a weighted matrix of the image data acquired at time $t_0$, a determination can be made what additional projections or what portions of the patient 22 may change over time that would require acquisition of additional image data of the patient 22 for a proper reconstruction. Accordingly, the weighted matrix can then be used to select the cells for powering of the emitter array 200.

In addition, a weighted matrix, which can include the one used in a determination of which cells to power, can also be used in the reconstruction. The weighted matrix can weight pixels in the image reconstruction based on recent image acquisitions and the previous image data. Thus, the reconstruction can include a blend of old image data for a pixel and image data acquired from a more recent projection rather than simply replacing the old image data with later acquired projection data.

After the cells are selected in block 422, the cells 204 can be powered individually and sequentially in block 426. Generally, a single cell 204 is powered for differentiation of image data acquired at the detector array 202. This can lead to the acquisition of image data at time $t_n$ in block 428. After the acquisition of the image data at time $t_n$, a determination block can determine whether further image data is selected or required in block 430. As discussed above, a three dimensional reconstruction of a portion of the patient 22 can be made and a determination can be made of whether an appropriate amount of image data has been acquired to form the reconstruction. Additionally or alternatively, the determination of whether additional image data is required in block 430 can be based upon the location of the device 60 in the image at the $t_n$ time, such as a position of the instrument 60 relative to an ablation site or if the device 60 is at an ablation site. If the device 60 is an ablation device and is positioned at the ablation site at the time $t_n$, further image data may not be selected in block 430. Accordingly, if no further image data is acquired, then a NO 432 path can be followed.

If it is selected that a reconstruction is to be formed, then a reconstruction can be made in block 434. Alternatively, or in addition thereto, simply a display of the acquired image data from any appropriate time, such as at time $t_n$, can be displayed in block 434. Display of the image data can be on any appropriate display, for example as illustrated as the image 76 on display 78. The image acquisition procedure that can then END at block 436. A surgical procedure, however, can continue such as an ablation of a portion of the patient 22. It can then be determined at a later time, to reenter the flow chart 400 to acquire image data of the patient 22 for further analysis, reconstruction, or for viewing additional portions of a surgical procedure (e.g. confirming an ablation or implant placement).

It will be also understood that if further image data is to be acquired or selected in block 430 then a YES path 450 can be followed to select a region of image analysis at time $t_0$ in block 406. It is understood that the acquired image data at time $t_n$ in a previous loop through the method 400 can become the image data at time $t_0$ when following the YES path 450. Accordingly, the method or process 400 can be understood to be a loop algorithm or procedure that can acquire image data and analyze image data as necessary or selected, such as by the user 23, to acquire an appropriate amount of image data.

As discussed above, a determination of whether an instrument is being used can be made in block 410. The discussion above relates to if an instrument is being used and the YES path 412 is followed. However, if an instrument is not being used then a NO path 460 can be followed. The NO path 460 can lead to detect a possible area of change in block 462 which can lead to an input of area of change into the exposure adjustment algorithm in block 464.

The detection of area of change in block 462 can be, for example, as illustrated in FIGS. 4A and 4B, a leading edge of a contrast agent wave. As illustrated in FIGS. 4A and 4B, the leading edge can be the area of change relative to the image data acquired at previous times. Generally, if image data is acquired of a region of the patient 22 that previously included the contrast agent, then additional image data regarding that region is not necessary as the configuration of the region having previously included the contrast agent will not substantially change over time. The detection of area of change can be based upon manual input by the user 22, automatic determination of the position of the leading front of the contrast agent (e.g. with image analysis based upon contrast data analysis, etc.), or other appropriate area of change detections. Also, the area of change can be based upon a comparison of recent or subsequent projections acquired of the subject that are compared to a prior version of the reconstructed model using the image data or directly with previous image projections. The current image data can include a sample of image projections acquired with a selected limited number of the cells 204. Thus, the comparison can compare image data between current and past images to determine where change is or is most likely to occur in the subject. These areas of change can be used to determine which cells to power for further image projection acquisition.

The input of the area of change to the exposure adjustment algorithm in block 462 can then be used to select cells 204 to power of the x-ray emitter array 200 in block 422. Again, the exposure adjustment algorithm can include an appropriate algorithm, such as a weighted matrix algorithm, to determine which additional cells of the emitter array 200 should be powered to acquire additional image data. For example, the selection can be used to determine which portion of the patient 22 should be imaged to acquire additional image data to form the appropriate reconstruction, if selected. Additionally, the selection of cells to be powered in the emitter array 200 can be based upon selecting cells 204 of the emitter array 200 that would generate x-rays relative to the patient 22 that would substantially only irradiate the patient 22 in the area where change will occur due to movement of the contrast agent to the patient 22.

After the selection of the cells in block 422 is made, the powering of the cells and other steps of the method 400 can be followed as discussed above. Accordingly, the determination of whether a device is being used in block 410 can be used to view the method 400 as two separate procedures for determining which portion of the present image data includes information that does not need to be imaged again, such as a current or passed position of the device or a current position of the contrast agent. The determination of what additional image data can be substantially similar, including determining or analyzing the portion of the image data or patient 22 that should be further imaged to acquire appropriate image data for a reconstruction, performing of a procedure, or the like.

Accordingly, the imaging device 20, including the emitter array 200 and the detector array 202, can be used to acquire image data of the patient 22. Although the emitter array 200 and the detector array 202 can be moved relative to the patient 22, movement of the emitter array 200 and detector array 202 may not be necessary to acquire a plurality of image projections relative to the patient 22 due to the plurality of displaced emitter array cells 204. The plurality of positions of the cells 204 can allow for a rapid and successive acquisition of different perspectives and projections of image data of the patient 22. Accordingly, the method in the flow chart 400 can be used to substantially automatically determine which emitter array cells 204 should be used to emit x-rays at a selected time to acquire additional or selected image data for various purposes, such as performance of a procedure, three dimensional reconstruction, or other appropriate procedures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of operating an emitter array comprising a plurality of x-ray emitting cells arranged in rows and columns, the method comprising:

selecting a first one or more of the plurality of x-ray emitting cells to emit first x-rays at a first region of a subject, wherein the subject includes a second region and a third region;

detecting the first x-rays and acquiring first image data of the subject corresponding to the detected first x-rays;

analyzing the first image data and detecting movement of a contrast agent within the subject including determining, due to movement of the contrast agent within the subject, (i) a contrast of the second region of the subject wherein the second region is a region that has changed due to the contrast agent and (ii) a contrast of the third region of the subject wherein the third region is a region that is likely to change;

based on the analysis of the first image data, determining (i) a location of the second region of the subject and (ii) a location of the third region of the subject;

based on and after determining the location of the second region and the determining the location of the third region, selecting a second one or more of the plurality of x-ray emitting cells to emit second x-rays towards at least one of the second region of the subject and the third region of the subject wherein the second x-rays are emitted after the first x-rays;

detecting the second x-rays and acquiring second image data of the subject corresponding to the second x-rays;

generating a weighted matrix for weighting portions of the first image data; and selecting the second one or more of the plurality of x-ray emitting cells based on the weighted matrix.

2. The method of claim 1, further comprising selecting a plurality of projections for generating a reconstruction of at least a portion of the subject, wherein the selecting of the second one or more of the plurality of x-ray emitting cells is based on determining which of the second one or more of the plurality of x-ray emitting cells is operable to obtain at least one of the selected plurality of projections.

3. The method of claim 2, further comprising displaying a two-dimensional image to represent a change over time of at least a portion of the subject based on the selected plurality of projections.

4. The method of claim 1, further comprising:

based on the first image data, determining a location of a leading front edge of the contrast agent in the subject; and based on the location of the leading front edge, selecting the second one or more of the plurality of x-ray emitting cells in the emitting array.

5. The method of claim 1, wherein:

the contrast of the second region of the subject is determined based on energy levels corresponding to the first image data; and the energy levels are based on a material composition within the second region.

6. The method of claim 1, further comprising:

operating a processor to analyze at least a portion of the first image data of the subject corresponding to the third region; and selecting the second one or more of the plurality of x-ray emitting cells based on the location of the third region.

7. The method of claim 1, further comprising:

while analyzing the first image data, determining, due to movement of the contrast agent within the subject, the contrast of the second region of the subject has changed;

based on the first image data, determining a location of the second region of the subject; and based on the location of the second region, selecting the second one or more of the x-ray emitting cells to emit second x-rays towards at least one of the second region and the third region.

8. The method of claim 1, further comprising:

while analyzing the first image data, determining, due to movement of the contrast agent within the subject, the contrast of the third region of the subject is likely to change;

based on the first image data, determining the location of the third region of the subject; and based on the location of the third region, selecting the second one or more of the x-ray emitting cells to emit second x-rays towards at least one of the second region and the third region.

9. The method of claim 1, further comprising, while analyzing the first image data, determining a contrast of the second region of the subject has changed and a contrast of the third region of the subject is likely to change, wherein:

the second region overlaps the first region; and the third region overlaps the second region.

10. The method of claim 1, wherein the selecting of the second one or more of the plurality of x-ray emitting cells includes selecting only ones of the plurality of x-ray emitting cells positioned to emit the second x-rays at the second region or the third region.

11. The method of claim 1, wherein:

while the first x-rays are being emitted from the first one or more of the plurality of x-ray emitting cells, x-rays are not emitted from other ones of the plurality of x-ray emitting cells; and while the second x-rays are being emitted from the second one or more of the plurality of x-ray emitting cells, x-rays are not emitted from other ones of the plurality of x-ray emitting cells.

12. A method of operating an emitter array comprising a plurality of x-ray emitting cells arranged in rows and columns, the method comprising:

selecting a first one or more of the plurality of x-ray emitting cells to emit first x-rays at a first region of a subject;

detecting the first x-rays and acquiring first image data of the subject corresponding to the first x-rays;

detecting movement of an instrument within the subject from a first location to a second location with a motion detection system;

determining the second location of the instrument within the subject;

based on the determined second location of the instrument within the subject, selecting a second one or more of the plurality of x-ray emitting cells to emit second x-rays at a second region of the subject, including, relating pixels in an image to the plurality of x-ray emitting cells, forming a weighted matrix of pixels of the first image data based on an identified region, and selecting the second one or more of the plurality of x-ray emitting cells based on a relationship of the pixels in the image to the plurality of x-ray emitting cells and the weighted matrix, wherein the second region includes the second location; and detecting the second x-rays and acquiring second image data of the subject corresponding to the second x-rays, wherein the second x-rays are emitted after the first x-rays.

13. The method of claim 12, further comprising: limiting the selection of the second one or more of the plurality of x-ray emitting cells to cells positioned to irradiate only a portion of the subject where the instrument is to pass including the second location of the instrument.

14. The method of claim 13, wherein detecting movement of the instrument within the subject from the first location to the second location includes:

determining a location of a leading end of the instrument by tracking a tracking device on the instrument with a tracking system; and based on the location of the leading end of the instrument, selecting the second one or more of the plurality of x-ray emitting cells.

15. The method of claim 14, further comprising tracking a tracking device associated with the instrument and within the subject, wherein:

the determining of the location of the leading end of the instrument includes determining a location of the tracking device; and selecting the second one or more of the plurality of x-ray emitting cells based on the location of the tracking device.

16. The method of claim 13, further comprising displaying an image based on the second image data acquired as a result of emitting the second x-rays from only the second one or more of the plurality of x-ray emitting cells.

17. The method of claim 13, further comprising displaying an image based on both the first image data and the second image data.

18. The method of claim 13, further comprising displaying a three-dimensional reconstruction of the subject based on at least one of the first image data or the second image data.

19. The method of claim 18, wherein the three-dimensional reconstruction of the subject is based on the first image data and the second image data.

20. The method of claim 12, identifying the regions for further image data acquisition based on the determined second location of the instrument.

21. A system to determine a location for acquiring second image data of a subject subsequent to acquiring first image data of the subject, the system comprising:

an exposure adjustment system having a processor operable to execute instructions to:

access the first image data of the subject;

relate pixels in the first image data to one or more of a plurality of x-ray emitting cells of an emitter array, wherein the plurality of x-ray emitting cells are arranged in rows and columns;

determine a location of a first region likely to change in the subject in and based on the accessed first image data;

identify a plurality of regions of the subject for acquisition of a second image data of the subject based on the determined location of the first region, wherein the plurality of regions include the first region in the first image data;

form a weighted matrix of pixels of the first image data based on the determined location of the first region likely to change;

based on the determined location of the first region likely to change and the formed weighted matrix of pixels of the first image data, select a second one or more of the plurality of x-ray emitting cells to emit x-rays through the plurality of regions; and receive the second image data based on detected x-rays emitted through the plurality of regions and acquiring the second image data corresponding to the x-rays emitted through the plurality of regions.

22. A method of operating an emitter array comprising a plurality of x-ray emitting cells arranged in rows and columns, the method comprising:

determining a location of at least one of:

(i) an edge of a region of contrast by analyzing an accessed first image data, wherein a moveable material within the subject causes the edge of the region of contrast or (ii) an instrument within the subject at least by tracking the instrument with a tracking device, separate from the first image data, associated with the instrument; and selecting one or more of the plurality of x-ray emitting cells based on at least all of:

(i) relating pixels in the first image data to the plurality of x-ray emitting cells, (ii) identifying regions of the subject for further image data acquisition based on the determined location of the instrument, (iii) forming a weighted matrix of pixels of the first image data based on the identified regions for further image data acquisition; and (iv) selecting the one or more of the plurality of x-ray emitting cells based on a relationship of the pixels in the first image data to the plurality of x-ray emitting cells and the determined location of the edge of the region of contrast using the formed weighted matrix.

23. The method of claim 22, further comprising: limiting the selection of the one or more of the plurality of x-ray emitting cells to cells positioned to irradiate only a portion of the subject where the movable material is to pass including the location of the edge of the region of contrast.

24. The method of claim 23, wherein the edge of the region of contrast is a leading edge of the region of contrast;

wherein the selecting of the one or more of the plurality of x-ray emitting cells further includes selecting one or more of the plurality of x-ray emitting cells based on the determined location of the instrument.

25. The method of claim 24, further comprising displaying an image based on second image data acquired as a result of emitting x-rays from only the selected one or more of the plurality of x-ray emitting cells.

26. The method of claim 24, further comprising:

determining a contrast of the region of contrast has changed;

in response to determining the contrast of the region of contrast has changed, selecting a second one or more of the plurality of x-ray emitting cells to emit x-rays;

emitting x-rays via the second one or more of the plurality of x-ray emitting cells at a second region;

generating second image data as a result of emitting x-rays from only the selected one or more of the plurality of x-ray emitting cells; and displaying an image based on both the first image data and the second image data, wherein the second image data corresponds to the second region of the subject for which contrast has changed.

27. The method of claim 26, wherein the displaying of the image based on both the first image data and the second image data includes displaying a three dimensional reconstruction of the subject based on the first image data and the second image data.

28. The system of claim 21, wherein the processor is operable to execute instructions to:

detect movement of a contrast agent from a first location to a second location;

detect movement of an instrument from a third location to a fourth location; and based on the second location of the contrast agent and the second location of the instrument and the fourth location of the instrument, select the second one or more of the plurality of x-ray emitting cells.

29. The system of claim 21, further comprising a navigation system operable to:

track a tracking device associated with an instrument to determine a location of at least a leading end of the instrument, wherein the determined location of the first region is a location of the leading end of the instrument; and transmit the determined location of the leading end of the instrument to the processor, wherein the determined location of the first region likely to change in the subject in the accessed first image data is based at least in part on the transmitted determined location of the leading end of the instrument.

30. The system of claim 29, wherein:

the navigation system comprises an electromagnetic localizer array;

the electromagnetic localizer array is operable to emit or sense an electromagnetic field from the tracking device;

the tracking device is an electromagnetic tracking device associated with the instrument; and the navigation system is configured to determine the location of the leading end of the instrument based on the emitted or sensed electromagnetic field.

31. The system of claim 21, further comprising an image analysis system operable to execute instructions to analyze the first image data to identify a region of a leading edge of a contrast medium in the first image data, wherein the leading edge of the contrast medium is the determined location of the first region.

32. The system of claim 21, wherein the processor is configured to update a volumetric three dimensional image based on a reconstruction weighted matrix of second image data to determine an updated volumetric three dimensional image including the first image data and the second image data.

* * * * *

UNITED STATES PATENT AND TRADEMARK OFFICE

CERTIFICATE OF CORRECTION

PATENT NO. : 10,849,574 B2
APPLICATION NO. : 13/166072
DATED : December 1, 2020
INVENTOR(S) : Patrick A. Helm et al.

It is certified that error appears in the above-identified patent and that said Letters Patent is hereby corrected as shown below:

On the Title Page

Page 2, Column 2, item [56], Line 11, Delete “Japanesse” and insert --Japanese-- therefor Page 2, Column 2, item [56], Line 33, Delete “Japanesse” and insert --Japanese-- therefor Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*